(12) United States Patent
Palazzotto et al.

(10) Patent No.: US 7,704,751 B2
(45) Date of Patent: Apr. 27, 2010

(54) POLYMERIC FLUORESCENT CHEMICAL SENSOR

(75) Inventors: Michael C. Palazzotto, Woodbury, MN (US); Neal A. Rakow, Woodbury, MN (US); Michael S. Wendland, North Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 854 days.

(21) Appl. No.: 11/552,825

(22) Filed: Oct. 25, 2006

(65) Prior Publication Data
US 2008/0070320 A1    Mar. 20, 2008

Related U.S. Application Data

(63) Continuation-in-part of application No. 11/522,559, filed on Sep. 18, 2006, now abandoned.

(51) Int. Cl.
*G01N 21/64* (2006.01)
*G01N 33/00* (2006.01)

(52) U.S. Cl. ............... 436/172; 436/106; 436/107; 436/111; 436/126; 436/127; 436/128; 436/129; 436/130; 436/131; 436/132; 436/139; 436/140; 436/141; 436/142; 436/166; 436/167; 436/181

(58) Field of Classification Search ......... 436/106–107, 436/111, 126–132, 139–142, 164, 166–167, 436/172, 181
See application file for complete search history.

(56) References Cited

U.S. PATENT DOCUMENTS

| | | | |
|---|---|---|---|
| 5,244,813 A * | 9/1993 | Walt et al. ............... | 436/172 |
| 5,411,709 A * | 5/1995 | Furuki et al. .............. | 422/91 |
| 5,882,774 A | 3/1999 | Jonza et al. | |
| 6,015,715 A | 1/2000 | Kirschner et al. | |
| 6,096,557 A * | 8/2000 | Tanaka et al. ............. | 436/100 |
| 6,296,927 B1 | 10/2001 | Jonza et al. | |
| 6,521,185 B1 * | 2/2003 | Groger et al. ............. | 422/82.08 |
| 6,613,421 B2 | 9/2003 | Jonza et al. | |
| 6,616,896 B2 | 9/2003 | Labuda et al. | |
| 6,623,973 B2 * | 9/2003 | Levitsky et al. ............. | 436/104 |
| 6,635,337 B2 | 10/2003 | Jonza et al. | |
| 6,815,211 B1 | 11/2004 | Blazewicz et al. | |
| 6,821,738 B2 * | 11/2004 | Harmon ................ | 435/7.1 |
| 6,998,271 B2 * | 2/2006 | Wong et al. .............. | 436/124 |
| 2002/0098120 A1 | 7/2002 | Blazewicz et al. | |
| 2003/0178607 A1 | 9/2003 | Swager et al. | |
| 2004/0092028 A1 | 5/2004 | Chaton et al. | |
| 2004/0184948 A1 | 9/2004 | Rakow et al. | |
| 2005/0059168 A1 | 3/2005 | Bazan et al. | |
| 2005/0147534 A1 | 7/2005 | Swager et al. | |
| 2005/0196775 A1 | 9/2005 | Swager et al. | |

FOREIGN PATENT DOCUMENTS

| | | |
|---|---|---|
| WO | WO2004/007634 | 1/2004 |
| WO | WO2005/012397 | 2/2005 |
| WO | WO2005/073338 | 8/2005 |

OTHER PUBLICATIONS

Budd, P. M. et al, Materials Today 2004, 7, 40-46.*
McKeown, N. B. et al, Chemistry A European Journal 2005, 11, 2610-2620.*
Pratibha Pandey and R.S. Chauhan, "Membranes for gas separation", Progress in Polymer Science, vol. 26, pp. 853-893, 2001.
Budd, Peter M., et al., "Polymers of intrinsic microporosity (PIMs): robust, solution-processable, organic nanoporous materials", *The Royal Society of Chemistry*, (2004) pp. 230-231.
Budd, Peter M., et al., "Solution-Processed, Organophilic Membrane Derived from a Polymer of Intrinsic Microporosity" *Advanced Materials*, (2004), vol. 16, No. 5, pp. 456-459.
Gregg, S.J. et al., "The Use of Gas Adsorption for the Determination of Surface Area and Pore Size Distribution", *Adsorption, Surface Area, and Porosity*, second edition, Academic Press, London (1982), pp. 283-286.

* cited by examiner

*Primary Examiner*—Arlen Soderquist
(74) *Attorney, Agent, or Firm*—Jean A. Lown

(57) ABSTRACT

A method of detecting organic vapors is described. More particularly, the method involves the use of an analyte sensor that contains a polymeric material having a relatively large intrinsic porosity and that is capable of fluorescence in the visible region of the electromagnetic spectrum. The method further includes exposing the analyte sensor to an environment that may contain an organic vapor and monitoring the analyte sensor for a change in a fluorescence signal. Although the organic vapor itself typically does not fluoresce in the visible wavelength range, presence of an organic vapor can alter the fluorescence signal of the analyte sensor.

20 Claims, No Drawings

POLYMERIC FLUORESCENT CHEMICAL SENSOR

CROSS REFERENCE TO RELATED APPLICATIONS

This application is a continuation in part of U.S. Ser. No. 11/522,559 filed on Sep. 18, 2006, now abandoned the disclosure of which is herein incorporated by reference.

TECHNICAL FIELD

A method of detecting the presence or absence of an organic vapor is described.

BACKGROUND

The development of robust sensors for a range of analytes remains an important endeavor for applications such as environmental monitoring. There is an ongoing need for sensors that can detect volatile organic compounds. Further, there is a continuing need for sensors that can be easily fabricated.

SUMMARY OF THE INVENTION

A method of detecting the presence or absence of an organic vapor is described. More specifically, a fluorescence signal of an analyte sensor containing a class of polymeric materials is measured before and after exposure or potential exposure to the organic vapor. A change in the fluorescence signal is indicative of exposure of the analyte sensor to an organic vapor. Suitable polymeric materials for use in the analyte sensor are those that emit a fluorescence signal in the visible region of the electromagnetic spectrum and that have a relatively large intrinsic porosity.

The method includes providing an analyte sensor containing a polymeric material having a unit of Formula I.

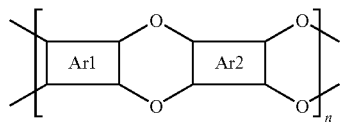

I

In Formula I, Ar1 includes a first aromatic group that is generally planar. Ar2 includes a second aromatic group and a third aromatic group connected to the second aromatic group though a contortion site such that the second aromatic group and the third aromatic group are not in the same plane. Ar1 and Ar2 are both fused to each other through a first 1,4-dioxane ring. The variable n is an integer equal to or greater than 1. The method further includes exposing the analyte sensor to an environment that may contain an organic vapor and monitoring the analyte sensor for a fluorescence signal change in the visible region of the electromagnetic spectrum upon exposure to the environment. A fluorescence signal change usually indicates exposure to the organic vapor.

The above summary of the present invention is not intended to describe each disclosed embodiment or every implementation of the present invention. The Detailed Description and Examples that follow more particularly exemplify these embodiments.

DETAILED DESCRIPTION OF THE INVENTION

A method of detecting organic vapors is described. More particularly, the method involves the use of an analyte sensor that contains a polymeric material having a relatively large intrinsic porosity and that is capable of fluorescence in the visible region of the electromagnetic spectrum. The method further includes exposing the analyte sensor to an environment that may contain an organic vapor and monitoring the analyte sensor for a change in a fluorescence signal. Although the organic vapor itself typically does not fluoresce in the visible wavelength range, the presence of an organic vapor can alter the fluorescence signal of the analyte sensor.

As used herein, the term "organic vapor" refers to an organic compound that has at least one carbon atom and at least one hydrogen or halogen atom. The organic vapor is typically an organic compound that is volatile at room temperature (i.e., a temperature in the range of about 20° C. to about 25° C.) and atmospheric pressure. The organic vapor often has a minimum partial pressure of 0.2 millitorr at 25° C.

The analyte sensor contains a polymeric material having at least one unit of Formula I.

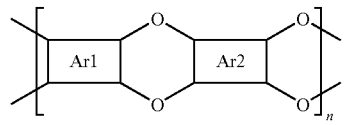

I

In Formula I, an aromatic ring of Ar1 and an aromatic ring of Ar2 are both fused to a first 1,4-dioxane ring. Group Ar1 includes a first aromatic group that is planar or generally planar. Group Ar2 includes a second aromatic group and a third aromatic group connected to the second aromatic group through a contortion site such that the second aromatic group and the third aromatic group are not in the same plane. Both the second aromatic group and the third aromatic group are attached to the contortion site. Each of the second aromatic group and the third aromatic group can be fused to the contortion site or can be attached to the contortion site through one chemical bond (e.g., single bond, double bond, or triple bond). The variable n in Formula I is an integer equal to or greater than 1. The polymeric material typically is not crosslinked.

Ar1 is a planar or generally planar aromatic group. In some embodiments, Ar1 is a single aromatic ring that is heterocyclic or carbocyclic. For example, Ar1 can be a benzene ring or a pyridine ring. A strong electron withdrawing group such as a cyano group or a nitro group can be attached to the aromatic ring. Other groups that can be attached to Ar1 include, but are not limited to, halogen groups and alkyl groups. The single aromatic ring is fused to the 1,4-dioxane ring as shown in Formula I.

In other embodiments, Ar1 contains multiple fused rings with at least one of the fused rings being aromatic. Any of the fused rings can be heterocyclic or carbocyclic. One or more of the rings can include, for example, a carbonyl group or sulfonyl group. A strong electron withdrawing group such as a cyano group or a nitro group can be attached to one or more of the aromatic rings included in Ar1. Other groups that can be attached to Ar1 include, but are not limited to, halogen groups and alkyl groups. If Ar1 has multiple fused rings, the ring fused to the 1,4-dioxane ring is aromatic.

Ar2 is a non-planar aromatic group that includes a second aromatic group and a third aromatic group. Both the second aromatic group and the third aromatic group are bonded to a common contortion site. That is, the second aromatic group and the third aromatic group of Ar2 are linked through the contortion site. Any molecular fragment, chemical bond, or single atom that connects the second aromatic group to the third aromatic group such that the second and third aromatic groups are not in the same plane can be used as the contortion site.

The second aromatic group and the third aromatic group of Ar2 each independently can be fused to the contortion site or connected to the contortion site with one chemical bond (i.e., single bond, double bond, or triple bond). The second aromatic group and the third aromatic group can each include one or more aromatic rings. Any of the aromatic rings can be carbocyclic or heterocyclic. Multiple aromatic rings are generally fused to each other. The one or more aromatic rings also can be fused to non-aromatic rings that can be carbocyclic or heterocyclic. A ring that is part of the second or third aromatic group can include a carbonyl group or sulfonyl group. Other groups that can be attached to Ar2 include, but are not limited to, halogen groups and alkyl groups. If the second aromatic group or the third aromatic group contains multiple fused rings, the ring attached to the contortion site is aromatic. Additionally, an aromatic ring of Ar2 is fused to the 1,4-dioxane ring in Formula I. In many embodiments of Formula I, an aromatic ring of the second aromatic group of Ar2 is fused to a first 1,4-dioxane ring and an aromatic ring of the third aromatic group of Ar2 is fused to a second 1,4-dioxane ring.

The polymeric material of Formula I, which is further described in WO 2005/012397 (McKeown et al.), can be prepared by reacting a first aromatic compound with a second aromatic compound through multiple nucleophilic substitution reactions. In some embodiments, a polymeric material containing a unit of Formula I can be prepared according to Reaction Scheme A. A first aromatic compound of Formula II having at least four halogen groups (i.e., X is a halogen group selected from fluoride, bromide, chloride, or iodide) can undergo multiple nucleophilic substitution reactions with a second aromatic compound of Formula III having at least four hydroxy groups.

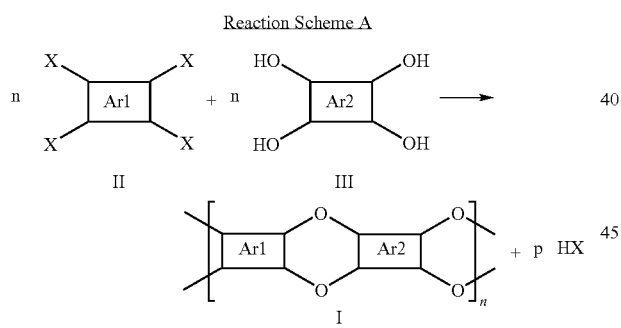

The first aromatic compound of Formula II in Reaction Scheme A typically has only one aromatic group, which can have a single or multiple ring structure, and the aromatic group tends to be planar or generally planar. That is, the first aromatic compound does not contain a contortion site. In some embodiments, the first aromatic compound includes a single aromatic ring that is carbocyclic or heterocyclic. In other embodiments, the first aromatic compound includes two or more fused rings with at least one of the rings being aromatic. Any of the fused rings can be carbocyclic or heterocyclic. The first aromatic compound has at least four halogen groups (i.e., fluoride, chloride, bromide, or iodide) that are arranged in pairs on the same or different aromatic rings. The halogen groups in each pair are attached to adjacent carbon atoms on the aromatic ring. When the first aromatic compound has more than one fused aromatic ring, the halogen pairs are often attached to distal (e.g., the outermost) aromatic rings. In some first aromatic compounds, a strong electron withdrawing group such as a cyano group or a nitro group can be attached to one or more of the aromatic rings. A ring that is part of the first aromatic group can include a carbonyl group or sulfonyl group. Some first aromatic compounds are substituted with an alkyl group or an additional halogen group.

Exemplary first aromatic compounds for Reaction Scheme A include, but are not limited to, benzene substituted with at least four halogen groups and an optional cyano or nitro group such as compounds of Formula IIa, IIb, IIc, IId, IIe, or IIf,

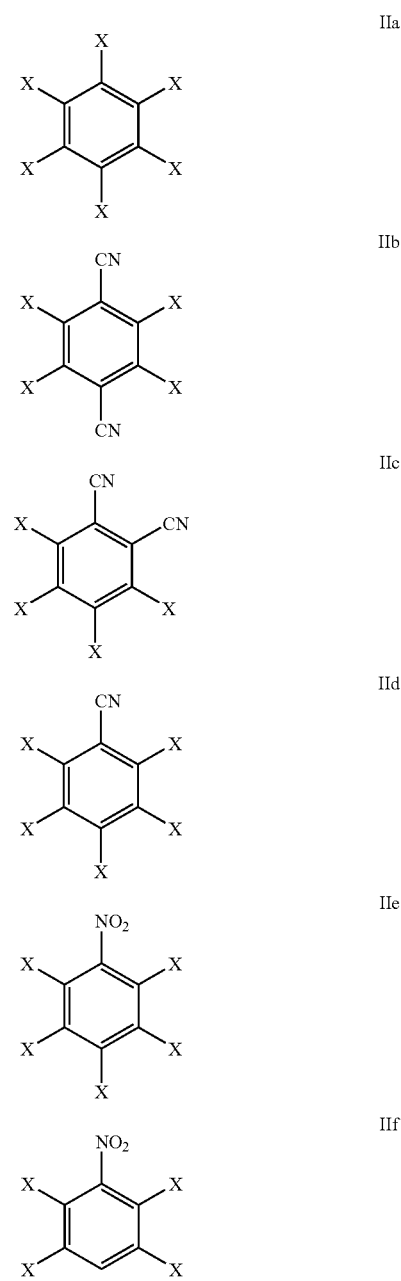

pyridine substituted with at least four halogen groups and an optional cyano or nitro group such as compounds of Formula IIg, IIh, or IIi;

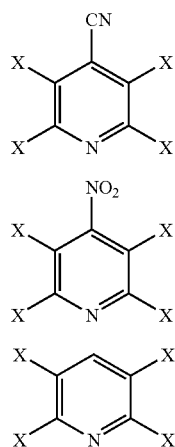

anthraquinone substituted with at least four halogen groups such as compounds of Formula IIj;

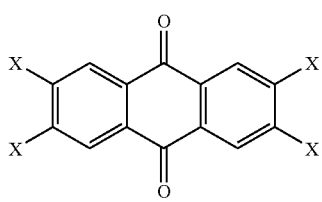

quinoxaline substituted with at least four halogen groups such as compounds of Formula IIk;

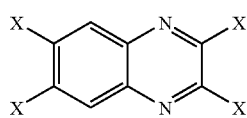

phenazine substituted with at least four halogen groups such as compounds of Formula Il:

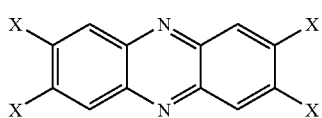

pyrazino[2,3-g]quinoxaline substituted with at least four halogen groups such as compounds of Formula IIm; or

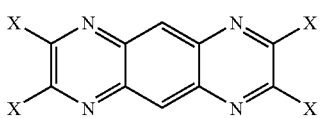

thianthrene 5,5,10,10-tetraoxide substituted with at least four halogen groups such as compounds of Formula IIn.

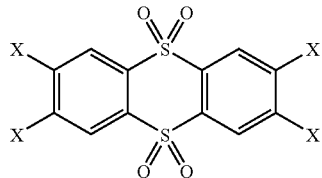

In these first aromatic compounds, the first aromatic group is considered to be equal to the compound minus four halogen groups. In these formulas, X is a halogen.

The first aromatic compound of Formula II in Reaction Scheme A is reacted with a second aromatic compound of Formula III. The second aromatic compound includes a second aromatic group, a third aromatic group, and a contortion site. The second aromatic group and the third aromatic group each have at least two hydroxy groups that are on adjacent carbon atoms of an aromatic ring. The second aromatic group and the third aromatic group of the second aromatic compound can each include one or more aromatic rings. Any of the aromatic rings can be carbocyclic or heterocyclic. Multiple aromatic rings are generally fused to each other. The one or more aromatic rings also can be fused to non-aromatic rings. The second aromatic group and the third aromatic group of the second aromatic compound are both attached to a common contortion site. The second and third aromatic groups each independently can be fused to the contortion site or connected with a one chemical bond (i.e., single bond, double bond, or triple bond) to the contortion site. Any molecular fragment, chemical bond, or single atom that connects the second aromatic group to the third aromatic group such that the second and third aromatic groups are not in the same plane can be used as the contortion site.

Both the second aromatic group and the third aromatic group of the second aromatic compound often contain a benzene ring that has at least two attached hydroxy groups on adjacent carbon atoms. These benzene rings of the second aromatic group and the third aromatic group are connected to each other through the contortion site. Some of the second aromatic compounds are substituted with an alkyl group.

Exemplary second aromatic compounds include, but are not limited to, compounds having both a second aromatic group and a third aromatic group fused to a spiroindane group such as a compound of Formula IIIa where $R^1$ is hydrogen or an alkyl;

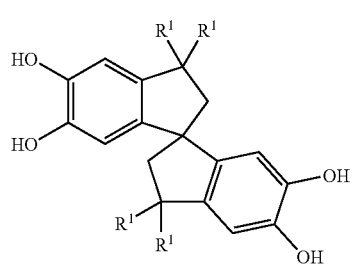

a second aromatic group and a third aromatic group attached to a fluorene such as a compound of Formula IIIb;

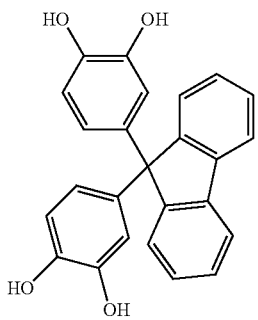
IIIb a second aromatic group and a third aromatic group both fused to a bicyclic octane group such as a compound of Formula IIIc where $R^1$ is hydrogen or alkyl;

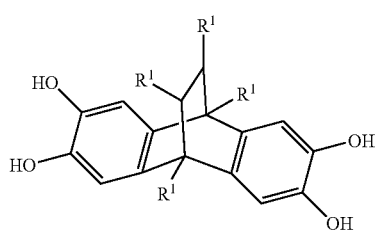
IIIc a second aromatic group and a third aromatic group both attached to a single benzene ring in a meta arrangement such as a compound of Formula IIId or IIIe;

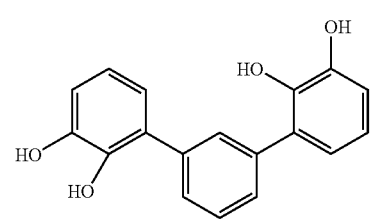
IIId

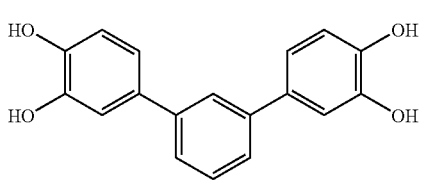
IIIe a second aromatic group and a third aromatic group attached to a central carbon atom that also has two attached phenyl groups such as a compound of Formula IIIf or IIIg;

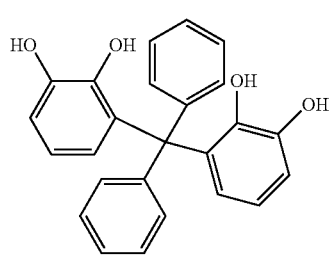
IIIf

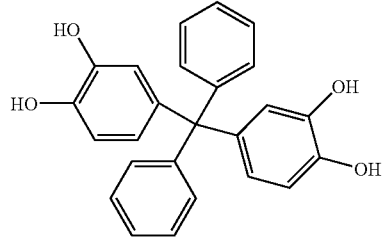
IIIg a second aromatic group and a third aromatic group attached by a single, chemical bond such as a biphenyl compound of Formula IIIh or IIIi or a binaphthyl compound of Formula IIIj; or

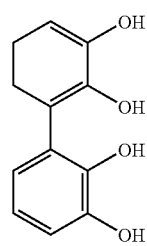
IIIh

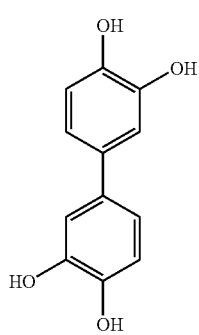
IIIi

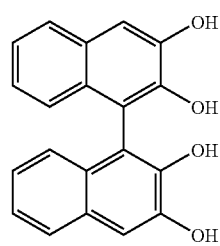
IIIj a second aromatic group and a third aromatic group attached to the same anthracen-diyl such as a compound of Formula IIIk.

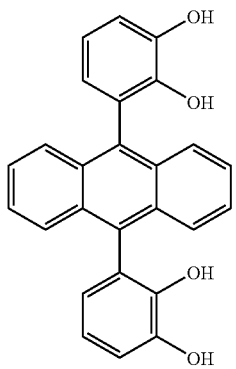

IIIk

In all of these second aromatic compounds, the second aromatic group and the third aromatic group is a benzene ring. Each of these benzene rings has at least two adjacent hydroxy groups. The remainder of the compound is considered to be equal to the contortion site.

If prepared using Reaction Scheme A, the polymeric material has a first and second end group. In some embodiments, the first and second end groups both include an aromatic group with at least two attached hydroxy groups. In other embodiments, the first and second end groups both include an aromatic group with at least two attached halogen groups. In still other embodiments, the first end group includes an aromatic group with at least two attached halogen groups and the second end group includes an aromatic group with at least two attached hydroxy groups. The end groups can often be selected by varying the molar ratio of the first aromatic compound to the second aromatic compound. That is, a molar excess of the first aromatic compound tends to favor end groups having halogen groups whereas a molar excess of the second aromatic compound tends to favor end groups having hydroxy groups. For example, when there is a molar excess of the first aromatic compound, the polymeric material can be of Formula Ia where X is a halogen and m is an integer equal to or greater than zero.

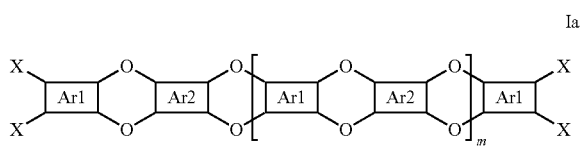

Ia

When there is a molar excess of the second aromatic compound, the polymeric material can be of Formula Ib where m is an integer equal to or greater than zero.

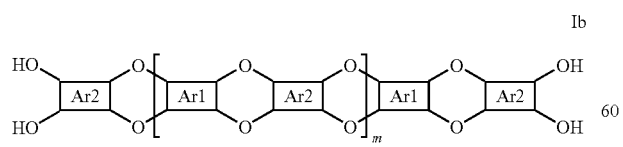

Ib

Ar1 and Ar2 are the same as described for Formula I.

As an alternative to Reaction Scheme A, the polymeric material of Formula I can be prepared according to Reaction Scheme B. A first aromatic compound of Formula IV having at least four hydroxy groups can undergo multiple nucleophilic substitution reactions with a second aromatic compound of Formula V having at least four halogen groups.

Reaction Scheme B

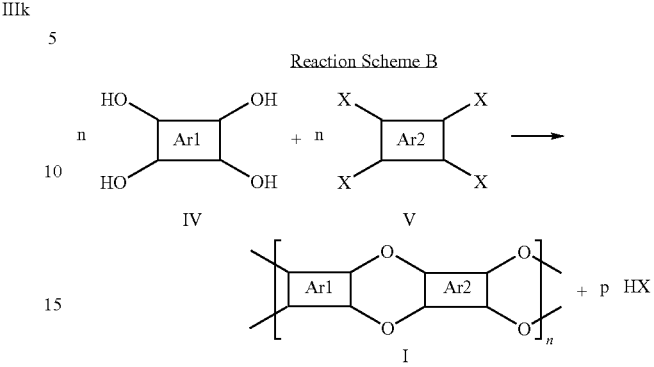

The first aromatic compound of Formula IV in Reaction Scheme B typically has only one aromatic group, which can have a single or multiple ring structure, and the aromatic group tends to be planar or generally planar. That is, the first aromatic compound does not contain a contortion site. In some embodiments, the first aromatic compound includes a single aromatic ring that is carbocyclic or heterocyclic. In other embodiments, the first aromatic compound includes two or more fused rings with at least one of the rings being aromatic. Any of the fused rings can be carbocyclic or heterocyclic. The first aromatic compound has at least four hydroxy groups that are arranged in pairs on the same or different aromatic rings. The hydroxy groups in each pair are attached to adjacent carbon atoms on the aromatic ring. When the first aromatic group has more than one fused aromatic ring, the hydroxy pairs are often attached to distal (e.g., the outermost) aromatic rings. A ring that is part of the first aromatic group can include carbonyl groups or sulfonyl groups. Some first aromatic compounds are substituted with an alkyl group.

Exemplary first aromatic compounds having at least four hydroxy groups include, but are not limited to, benzene substituted with at least four hydroxy groups such as a compound of Formula IVa;

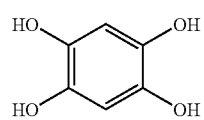

IVa

[1,4]benzoquinone substituted with at least four hydroxy groups such as a compound of Formula IVb;

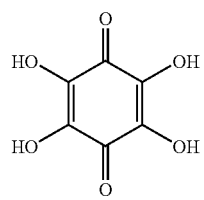

IVb triphenylene substituted with at least four hydroxy groups such as a compound of Formula IVc;

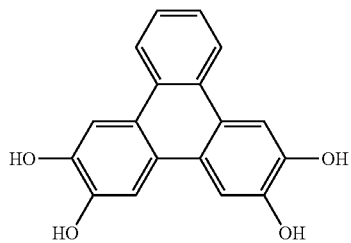

IVc anthaquinone substituted with at least four hydroxy groups such as a compound of Formula IVd;

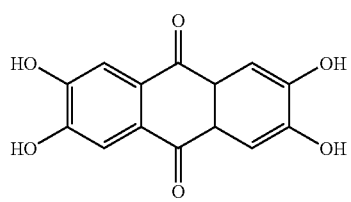

IVd anthracene substituted with at least four hydroxy groups such as a compound of Formula IVe where $R^1$ is hydrogen or alkyl;

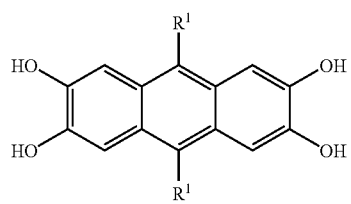

IVe 10,12-dihydro-indeno[2,1-b]fluorene substituted with at least four hydroxy groups such as a compound of Formula IVf where $R^1$ is hydrogen or alkyl; or

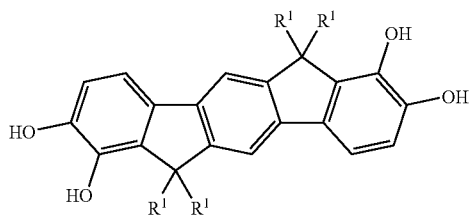

IVf a compound of Formula IVg or IVh where $R^1$ is hydrogen or alkyl.

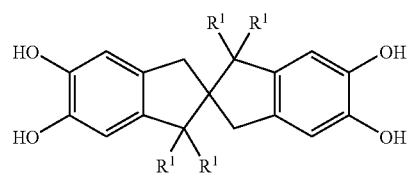

IVg

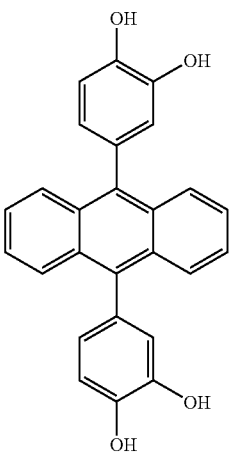

IVh

In all of these first aromatic compounds, the first aromatic group is considered to be equal to the compound minus four hydroxy groups.

The first aromatic compound of Formula IV in Reaction Scheme B is reacted with a second aromatic compound of Formula V. The second aromatic compound includes a second aromatic group, a third aromatic group, and a contortion site. The second aromatic group and the third aromatic group each have at least two halogen groups that are on adjacent carbon atoms of an aromatic ring. The second aromatic group and the third aromatic group of the second aromatic compound can each include one or more aromatic rings. Any of the aromatic rings can be carbocyclic or heterocyclic. Multiple aromatic rings are generally fused to each other. The one or more aromatic rings can be fused to additional non-aromatic rings. The second aromatic group and the third aromatic group of the second aromatic compound are both attached to a common contortion site. The second and third aromatic groups each independently can be fused to the contortion site or connected with a one chemical bond (i.e., single bond, double bond, or triple bond) to the contortion site. Any molecular fragment, chemical bond, or single atom that connects the second aromatic group to the third aromatic group such that the second and third aromatic groups are not in the same plane can be used as the contortion site.

Both the second aromatic group and the third aromatic group often contain a benzene ring that has at least two attached halogen groups on adjacent carbon atoms. These benzene rings of the second aromatic group and the third aromatic group of the second aromatic compound are connected to each other through the contortion site. Some second aromatic compounds are substituted with an alkyl group.

Exemplary second aromatic compounds include, but are not limited to, compounds having a central carbon atom that also has two attached phenyl groups and two aromatic groups each having at least two halogen groups such as compounds of Formula Va where each X is a halogen.

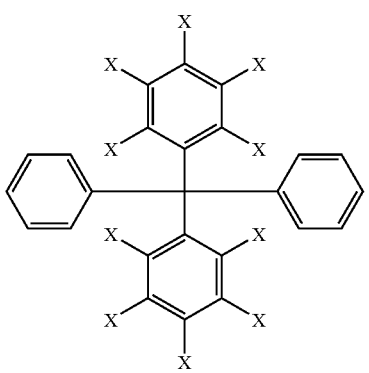

Va

In this compound, the second and third aromatic groups are benzene rings substituted with halogen groups. The contortion site is equal to the compound minus the two benzene rings that are substituted with halogen groups.

If prepared using Reaction Scheme B, the polymeric material has a first and second end group. In some embodiments, the first and second end groups both include an aromatic group with at least two attached hydroxy groups. In other embodiments, the first and second end groups both include an aromatic group with at least two attached halogen groups. In still other embodiments, the first end group includes an aromatic group with at least two attached hydroxy groups and the second end group includes an aromatic group with at least two attached halogen groups. The end groups can often be selected by varying the molar ratio of the first aromatic compound to the second aromatic compound in Reaction Scheme B. That is, a molar excess of the first aromatic compound tends to favor end groups having hydroxy groups whereas a molar excess of the second aromatic compound tends to favor end groups having halogen groups. For example, when there is a molar excess of the first aromatic compound, the polymeric material can have a Formula Ic where m is an integer equal to or greater than zero.

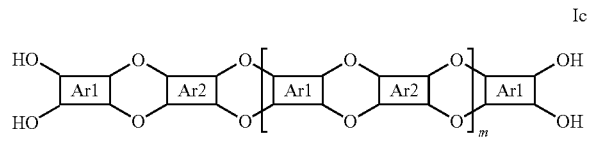

Ic

When there is a molar excess of the second aromatic compound, the polymeric material can have a Formula Id where X is a halogen and m is an integer equal to or greater than zero.

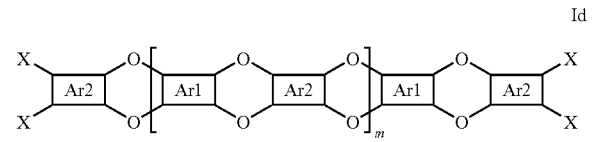

Id

Ar1 and Ar2 are the same as described for Formula I.

The polymeric material containing a unit of Formula I has an intrinsic porosity due primarily to the presence of the contortion sites in Ar2. Because of its fairly rigid and contorted molecular structure, the polymeric material is typically unable to pack efficiently resulting in the formation of pores.

As used herein, the term "intrinsic porosity" means that the polymeric material has a pore volume of at least 0.1 mL/g, at least 0.2 mL/g, or at least 0.5 mL/g as measured by nitrogen adsorption under cryogenic conditions using the methods developed by Barret, Joyner, and Halenda (BJH method) or by Horvath and Kawazoe. These methods are described, for example, by S. J. Gregg and S. W. Sing in *Adsorption, Surface Area, and Porosity*, second edition, Academic Press, London (1982). Typically, the polymeric material has at least 25 percent, at least 50 percent, or at least 75 percent of the total pore volume, as measured by nitrogen adsorption, resulting from pores in a range of 0.3 to 20 nanometers or in the range of 2 to 10 nanometers.

The polymeric material has a surface area of at least 300 $m^2/g$. The surface area is typically measured by nitrogen adsorption under cryogenic conditions using the BET (Brunauer-Emmett-Teller) method, which is described in the above cited reference by Gregg and Sing. For some polymeric materials, the surface area is at least 350 $m^2/g$, at least 400 $m^2/g$, at least 500 $m^2/g$, or at least 600 $m^2/g$. The surface area can often be up to 800 $m^2/g$, up to 900 $m^2/g$, up to 1000 $m^2/g$, up to 1100 $m^2/g$, or up to 1200 $m^2/g$. That is, the surface area is often in the range of 300 to 1200 $m^2/g$, in the range of 300 to 1000 $m^2/g$, in the range of 400 to 1000 $m^2/g$, or in the range of 500 to 1000 $m^2/g$.

In some embodiments, the polymeric material containing the unit of Formula I can be in the form of a powder such as, for example, in the form of a pressed powder. In other embodiments, the polymeric material containing a unit of Formula I can be in the form of a film. That is, the analyte sensor includes a film of the polymeric material containing a unit of Formula I. Any suitable film thickness can be used. Films can be formed, for example, by solvent casting techniques such as spin coating, dip coating, bar coating, slotted dye coating, and extrusion coating. More specifically, the polymeric material can be dissolved in a suitable solvent to form a solution. Suitable solvents include, but are not limited to, tetrahydrofuran, cyclohexene oxide, dimethylformamide, dimethylacetamide, tetrahydropyran, and chlorobenzene. The solution can be spread on a support surface and then the solvent can be evaporated to form a film. Any suitable polymeric or inorganic support can be used. After evaporation of the solvent, the film can be removed from the support.

In still other embodiments, the polymeric material containing a unit of Formula I can be in the form of a coating adjacent to another layer. For example, the coating can be adhered to the other layer. Any suitable coating thickness can be used. In some embodiments, the other layer is a support substrate. The polymeric material can be in contact with a support substrate or can be separated from the support substrate by one or more additional layers such as a tie layer or a reflective layer. Suitable techniques for forming a coating include, but are not limited to, printing, spin coating, dip coating, bar coating, slotted dye coating, and extrusion coating.

A support substrate can be formed from any suitable material capable of providing support for the polymeric material containing a unit of Formula I. The support substrate may be flexible or non-flexible (e.g., rigid), and may be tailored for a given application. The support substrate may have a thickness that varies depending on a given application. The support substrate often has a thickness of at least about 50 micrometers and typically extends up to about 25 millimeters. Suitable materials for forming the support substrate include, but are not limited to, a polymer film or sheet (e.g., a polyethylene terephthalate (PET) or polycarbonate film), a glass substrate, an inorganic substrate such as a ceramic substrate or a silicon wafer or metallic substrate, a fabric sheet, or any combination thereof.

In some embodiments, the support substrate includes a reflective surface. The reflective surface can be adjacent to the polymeric material containing a unit of Formula I or can be separated from this polymeric material by one or more layers such as a tie layer or an adhesive layer. The reflective surface may be a substantially continuous reflective surface or a discontinuous reflective surface. Further, the reflective surface may include one or more reflective layers. Desirably, the reflective surface contains a single, continuous reflective surface forming an outer surface of the support substrate or a single, continuous reflective layer on an outer surface of the support substrate.

The reflective surface can be the outer surface of a single layer support substrate such as a silicon wafer or can be an outer surface of a multilayer, all-polymeric, birefringent optical film such as those disclosed, for example, in U.S. Pat. No. 6,635,337 (Jonza et al.); U.S. Pat. No. 6,613,421 (Jonza et al.); U.S. Pat. No. 6,296,927 (Jonza et al.); and U.S. Pat. No. 5,882,774 (Jonza et al.), all of which are incorporated herein by reference.

Alternatively, the reflective surface can be the outer surface of a reflective layer disposed on a support substrate that has little or no reflectivity. The reflective layer can be a metallic or semi-metallic layer. Suitable materials for the reflective layer include, but are not limited to, metals or semi-metals such as aluminum, chromium, gold, palladium, platinum, titanium, nickel, silicon, silver, and combinations thereof. Alloys such as gold/palladium or nickel/chromium may also be used. Other suitable materials include metal oxides such as, for example, aluminum oxide, silicon oxide, chromium oxide, titanium oxide, and combinations thereof. Still other suitable materials include metal nitrides such as, for example, silicon nitride, aluminum nitride, titanium nitride, chromium nitride, carbon nitride, and combinations thereof. When present as a layer separate from the support substrate, the reflective layer can have any suitable thickness. The average reflective layer thickness often has a thickness of at least at least 10 nanometers, at least 20 nanometers, at least 25 nanometers, or at least 50 nanometers. This thickness often extends up to 100 nanometers, up to 200 nanometers, or greater.

In some exemplary embodiments, the reflective surface is at least 90 percent reflective, at least 95 percent reflective, at least 98 percent reflective, or at least 99 percent reflective. In other exemplary embodiments, the reflective surface is semi-reflective, wherein the reflective surface is in the range of 20 to 90 percent reflective, in the range of 30 to 90 percent reflective, in the range of 20 to 70 percent reflective, or in the range of 30 to 70 percent reflective.

The polymeric materials containing a unit of Formula I tend to emit a fluorescence signal in the visible region of the electromagnetic spectrum. As used herein, the term "visible region" of the electromagnetic spectrum refers to radiation having a wavelength in the range of about 400 to about 1000 nanometers, in the range of about 400 to about 900 nanometers, or in the range of about 400 to about 800 nanometers. As used herein, the term "fluorescence" refers to the emission of electromagnetic radiation resulting from an electronic transition from an excited electronic state of a given spin to a lower energy electronic state of the same spin state such as from a singlet to another singlet state. The fluorescence signal is due, at least in part, to the extensive fusion of aromatic rings in the polymeric material. The first aromatic group is fused to the second aromatic group through a 1,4-dioxane ring. The first aromatic group is often fused through a second 1,4-dioxane ring to another second aromatic group or to a third aromatic group as in Formulas Ia, Ib, Ic, and Id.

Although not wanting to be bound by theory, the polymeric material having a relatively large intrinsic porosity tends to sorb (i.e., adsorb or absorb) organic vapors when exposed to an environment containing such organic vapors. The sorption (i.e., absorption or adsorption) of the organic vapors can affect the inter-chain and intra-chain interactions of the polymeric materials containing a unit of Formula I. A change in these interactions can alter the fluorescence signal emitted by the polymeric materials in the visible region of the electromagnetic spectrum indicating exposure to the organic vapors. The intensity of the fluorescence signal can increase or decrease. Additionally, the spectrum, which is a plot of the intensity of the fluorescence as a function of wavelength, can be changed. For example, the wavelength of maximum fluorescence can be shifted to a longer to shorter wavelength.

The organic vapors themselves typically do not emit a fluorescence signal in the visible wavelength range. Advantageously, no additional chromophore is needed for detection of the organic vapors using the analyte sensor. That is, the organic vapor is typically not bonded to an additional chromophore for detection. Rather, detection is based on interaction of the organic vapor with the polymeric material contained in the analyte sensor.

When the environment contains a single organic vapor, the change in fluorescence signal can be correlated to the concentration of the organic vapor in the environment. A calibration curve, which is a plot of concentration versus fluorescence signal, can be prepared by exposing the analyte sensor to various known concentrations of the organic vapor. The sample fluorescence signal can be measured and compared to the calibration curve to determine the organic vapor concentration.

Some organic vapors tend to increase the fluorescence signal emitted by the polymeric material containing a unit of Formula I. Although organic vapors that increase the fluorescence signal can include a cyano (—CN) group, these volatile organic compounds usually are free of other types of strong withdrawing groups such as a nitro group. Additionally, these organic vapors are often organic compounds that lack a strong electron donating group such as an amino group. Many exemplary organic vapors that increase the fluorescence signal emitted by the polymeric material are volatile organic compounds that are associated with industrial processes. These volatile organic compounds include, but are not limited to, ketones such as acetone and methyl ethyl ketone; aldehydes such as formaldehyde; ethers such as tetrahydrofuran and diethyl ether; esters such as ethyl acetate; alcohols such as methanol, ethanol, and isopropanol; alkanes such as methane, ethane, propane, butane, and heptane; substituted alkanes such as halogenated alkanes; benzene; substituted benzenes such as benzene substituted with an alkyl (e.g., toluene or mesitylene), halogen (e.g., chlorobenzene or bromobenzene), or combination thereof; and nitriles such as acetonitrile.

Other organic vapors tend to decrease the fluorescence signal emitted by the polymeric material containing a unit of Formula I. Exemplary organic vapors that decrease the fluorescence signal emitted by the polymeric material include volatile organic compounds that contain a strong electron withdrawing group other than a cyano group or a strong electron donating groups. More particularly, volatile organic compounds that contain a strong electron donating group such as an amino group or a strong electron withdrawing group such as a nitro group tend to decrease the fluorescence signal emitted by the polymeric material. These organic vapors include, but are not limited to, anilines such as N,N-dialkylaniline (e.g., N,N-dimethylaniline) or trialkylaniline (e.g., tripropylaniline); toluidines such as N,N-dialkyl-p-toluidine (N,N-dimethyl-p-toluidine); nitrobenzenes; nitrotoluenes such as 2,4-dinitrotoluene or trinitrotoluene; and biogenic amines such as putrescine, cadaverine, tyramine, histamine, spermidine, and spermine.

It is unexpected that the same analyte sensor can be used to monitor the presence of such a diverse range of volatile organic compounds. The fluorescence signal can increase or decrease depending on the type of organic vapor present and the direction of the fluorescence change can be used to help identify the nature of the organic vapor responsible for the fluorescence change. Many volatile organic compounds commonly used in industrial processes increase the fluorescence signal while some other volatile organic compounds not commonly associated with industrial processes such as amino-containing compounds and nitro-containing compounds decrease the fluorescence signal.

Unlike known analyte sensors based on a fluorescent measurement such as those described in U.S. Patent Application 2005/0059168 (Bazan et al.), there is no need for a separate sensing molecule and reporting molecule. Rather, the polymeric material that contains a unit of Formula I can function as both the sensing molecule and reporting molecule. A separate chromophore is not attached to the organic vapors for detection purposes.

Unlike known analyte sensors based on a fluorescent measurement, the fluorescence signal of the polymeric material containing a unit of Formula I can be quenched by organic vapors having either a strong electron withdrawing group or a strong electron donating group. In contrast, patent application WO 2005/07338 (Rosler et al.) reports that typical organic sensory polymers do not respond to electron donating materials.

Unlike known analyte sensors based on a fluorescent measurement, the fluorescence signal can increase in the presence of many volatile organic compounds. An increase in the fluorescence signal is unusual because most detection schemes are based on fluorescence quenching rather than fluorescence enhancement.

Several approaches can be used to monitor a change in the fluorescence signal of the analyte sensor upon exposure to an environment that may contain an organic vapor. In one approach, a first sensor is used as a sample sensor and a second sensor is used as a reference sensor. The sample sensor is identical or almost identical to the reference sensor before exposure to the environment that may contain an organic vapor. The sample sensor is subjected to the environment but the reference sample is not. However, it may be desirable to subject the reference sensor and the sample sensor to the same relative humidity. A change in the fluorescence signal can be monitored by (a) measuring a reference fluorescence signal for the reference sensor that is not exposed to the environment, (b) measuring a sample fluorescence signal after exposing the sample sensor to the environment, and (c) subtracting the reference fluorescence signal from the sample fluorescence signal. Alternatively, a change in the fluorescence signal can be monitored by (a) measuring a reference fluorescence signal for the reference sensor that is not exposed to the environment, (b) measuring a sample fluorescence signal after exposing the sample sensor to the environment, and (c) dividing the sample fluorescence signal by the reference fluorescence signal.

In another approach, a single sensor is used. A change in the fluorescence signal can also be monitored by (a) measuring a reference fluorescence signal prior to exposing the sensor to the environment, (b) measuring a sample fluorescence signal after exposing the same sensor to the environment, and (c) subtracting the reference fluorescence signal from the sample fluorescence signal. Alternatively, a change in the fluorescence signal can be monitored by (a) measuring a reference fluorescence signal prior to exposing the sensor to the environment, (b) measuring a sample fluorescence signal after exposing the same sensor to the environment, and (c) dividing the sample fluorescence signal by the reference fluorescence signal.

The fluorescence signal of the sensor is in the visible region of the electromagnetic spectrum and can be detected by any suitable means such as the human eye or a photodetector. In many applications, a photodetector is preferred because lower concentrations can be detected and the results can be quantified. For example, some polymeric materials containing a unit of Formula I have a green or yellowish-green fluorescence that can be observed by the human eye. The intensity of the fluorescence can increase or decrease upon exposure of the analyte sensor to an environment that contains an organic vapor such as a vapor from an organic solvent. The excitation of the analyte sensor to produce a fluorescence signal can be from natural light or can be from any suitable light source that includes wavelengths that result in the fluorescence signal in the visible region of the electromagnetic spectrum.

A light source is often used to radiate the analyte sensor. The light source can be a visible light source, an ultraviolet light source, or both a visible/ultraviolet light source. A photodetector is often arranged to measure the fluorescence signal. The detector is typically arranged to measure the amount of radiation emitted by the analyte sensor rather than the amount of radiation absorbed or transmitted by the analyte sensor. The light source, sensor, and photodetector are arranged to form an angle less than 180 degrees. For example, the angle is often close to about 90 degrees.

The fluorescence signal can be measured at a single wavelength or at a range of wavelengths in the visible region of the electromagnetic spectrum. A change in the fluorescence spectrum in the visible range can, at least in some instances, be used to identify the composition of the organic vapor. For example, the fluorescence at various wavelengths can be measured under constant excitation conditions. The constant excitation conditions can be from a light source that provides a single wavelength, a narrow range of wavelengths, or a broad range of wavelengths. Alternatively, a change in the excitation spectrum can be used, at least in some instances, to identify the composition of the organic vapor. For example, the fluorescence signal from a single wavelength or wavelength range can be monitored as a function of the excitation wavelength.

The detection method can be reversible for some organic vapors. For example, some organic vapors can be removed from the polymeric material having intrinsic porosity by purging with nitrogen. Many common organic solvents that lack an amino or nitro group can be removed from the polymeric material by purging with nitrogen. The removal of the organic vapor tends to return the fluorescence signal of the polymeric material to a condition identical or nearly identical to that prior to sorption of the organic vapor.

EXAMPLES

These examples are for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Nitrobenzene was obtained from Avocado Research Chemicals a unit of Alfa-Aesar, Ward Hill, Mass.

Acetonitrile, acetone, ethyl acetate, methyl ethyl ketone, toluene, isopropyl alcohol, heptane, and tetrahydrofuran were obtained from EMD Chemicals Inc., Gibbstown, N.J.

Bromobenzene, chlorobenzene, N,N-dimethylaniline, mesitylene, and tripropylamine were obtained from Sigma-Aldrich Corp., St. Louis, Mo.

SUBA-SEAL septa were available from William Freeman Ltd., South Yorkshire, United Kingdom.

Fluorescence Measurements

The fluorescence measurements were made with a SPEX Fluorolog Spectrometer available from Spex Industries, Edison, N.J., equipped with a Model 1681 excitation monochromator having a path length of 0.22 meters and a Model 1680 double emission monochromator having a path length of 0.22 meters. All entrance and exit slits were set at 1.0 mm, and the excitation wavelength was set at 400 nm for the emission scan. The intensity of the emission peak maximum, which generally occurs in the 490 to 510 nm region for these settings, was followed. The changes in the fluorescence intensity at peak maximum were determined using GRAMS software from Thermo Electron Corporation, Thermo Electron Corporation, Waltham, Mass. The peak intensity was read off the cursor positioned at the peak maximum.

For Test Method 1, the scan rate was 1 nm/point and 1 second/point. For Test Method 2, the scan rate was 2 nm/point and 0.1 second/point. The polymeric material was oriented such that it bisected the angle between the excitation and emission apertures of the spectrometers. This arrangement minimizes light scatter into the detector.

Preparation of Polymeric Material A

A polymeric material that contained units of Formula I was prepared from the monomers 5,5',6,6'-tetrahydroxy-3,3,3',3'-tetramethyl-1,1'-spirobisindane (BC) and tetrafluoroterephthalonitrile (FA). The synthesis procedure was reported by Budd et al., in *Advanced Materials,* 2004, Vol. 16, No. 5, pp. 456-459. BC (10.25 grams) was combined with of FA (6.02 grams), potassium carbonate (25.7 grams), and 200 milliliters of N,N-dimethylformamide. The mixture was reacted at 65° C. for 72 hours. The resulting polymer was dissolved in tetrahydrofuran, precipitated three times from methanol, and then dried under vacuum at room temperature to obtain a yellow solid product with a weight average molecular weight (Mw) of 73,900 grams/mole.

Analyte Sensor 1

Polymeric Material A was then spin-coated (Spin Coater Model EC101 from Headway Research, Inc., Garland, Tex.) onto several 50×75 mm glass slides at 1000 rpm for 30 seconds using a 5 weight % solution of Polymeric Material A in cyclohexene oxide to give a dry film thickness of about 1000 nm. Using a glass cutter, samples having dimensions of approximately 7×50 mm were cut from the larger slides.

These smaller samples were placed in an 8 ml glass vial using a small amount of cotton at the bottom to support the sample and a SUBA-SEAL Septum No. 4 at the top to seal the vial. There was a slot cut in the rubber septum to hold the sample in position. The septum allowed for the containment of the solvent vapors inside the vial and the cotton kept the bottom of the sample from dipping in any solvent that might pool in the bottom of the vial. An aliquot of the analyte was added to the vial (0.1 to 0.2 mL), making sure that the analyte did not touch the surface of the slide.

Analyte Sensor 2

This configuration was devised to further minimize sample movement during subsequent measurements. Polymeric Material A was spin-coated (Spin Coater Model EC101 from Headway Research, Inc., Garland, Tex.) onto several 50×75 mm glass slides at 1800 rpm for 30 seconds using a 4 weight % solution of Polymeric Material A in tetrahydropyran to give a dry film thickness of about 500 nm. Samples having dimensions of approximately 7×30 mm were cut from the larger slides.

These smaller samples were placed in a 1 cm×1 cm quartz cuvette using triangular TEFLON blocks to hold the sample in a vertical position and a SUBA-SEAL Septum No. 4 to seal the top of the cuvette. The septum allowed for the containment of the solvent vapors inside the cuvette. The analyte was added by injecting 2 ml of vapor obtained from the headspace of the analyte container using a disposable syringe.

Monitoring Changes in Fluorescence Signal

Tests were conducted by scanning the emission, prior to addition of the analyte, in the visible region (Scan 1, time 0 minutes) and measuring the maximum peak intensity, which generally occurs in the range of 490 to 510 nm. After addition of the analyte, successive emission scans were taken to record the changes in the intensity of the peak with time as the solvent vapor concentration increased in the vial. The end of the test was indicated by successive scans showing very little change in the intensity of the peak.

Example 1

Analyte Sensor 1 was exposed to nitrobenzene. The fluorescence signal was measured using Test Method 1. The emission intensity at the peak maximum was recorded as a function of time and is shown in Table 1.

TABLE 1

| Scan # | Time (min) | Intensity Peak Maximum |
|---|---|---|
| 1 | 0 | 1851898 |
| 2 | 0.5 | 2106501 |
| 3 | 6.5 | 69701 |
| 4 | 12.5 | 40443 |
| 5 | 23.5 | 27421 |

Example 2

Analyte Sensor 2 was exposed to nitrobenzene. The fluorescence signal was measured using Test Method 2. The emission intensity at the peak maximum was recorded as a function of time and is shown in Table 2.

TABLE 2

| Scan # | Time (min) | Intensity Peak Maximum |
|---|---|---|
| 1 | 0 | 2494720 |
| 2 | 0.5 | 1327040 |
| 3 | 2.5 | 992710 |
| 4 | 4.5 | 861400 |
| 5 | 5.5 | 767510 |
| 6 | 7.5 | 709200 |
| 7 | 9.5 | 656860 |
| 8 | 13.5 | 629590 |

Example 3

Analyte Sensor 1 was exposed to N,N-dimethylaniline. The fluorescence signal was measured using Test Method 1. The emission intensity at the peak maximum was recorded as a function of time and is shown in Table 3.

TABLE 3

| Scan # | Time (min) | Intensity Peak Maximum |
|---|---|---|
| 1 | 0 | 5279156 |
| 2 | 0.5 | 4453651 |
| 3 | 3.5 | 373914 |
| 4 | 6.5 | 43725 |
| 5 | 12.5 | 26998 |
| 6 | 24.5 | 18442 |

Example 4

Analyte Sensor 2 was exposed to N,N-dimethylaniline, The fluorescence signal was measured using Test Method 2. The emission intensity at the peak maximum was recorded as a function of time and is shown in Table 4.

TABLE 4

| Scan # | Time (min) | Intensity Peak Maximum |
| --- | --- | --- |
| 1 | 0 | 2559330 |
| 2 | 0.5 | 961730 |
| 3 | 2.5 | 893120 |
| 4 | 3.5 | 880230 |
| 5 | 6.5 | 872970 |

Example 5

Analyte Sensor 1 was exposed to tetrahydrofuran. The fluorescence signal was measured using Test Method 1. The emission intensity at the peak maximum was recorded as a function of time and is shown in Table 5.

TABLE 5

| Scan # | Time (min) | Intensity Peak Maximum |
| --- | --- | --- |
| 1 | 0 | 1093733 |
| 2 | 0.5 | 5427505 |
| 3 | 4.5 | 6238854 |
| 4 | 18.5 | 7197287 |

Example 6

Analyte Sensor 1 was exposed to toluene. The fluorescence signal was measured using Test Method 1. The emission intensity at the peak maximum was recorded as a function of time and is shown in Table 6.

TABLE 6

| Scan # | Time (min) | Intensity Peak Maximum |
| --- | --- | --- |
| 1 | 0 | 3200946 |
| 2 | 0.5 | 5511502 |
| 3 | 6.5 | 6201994 |
| 4 | 18.5 | 6567851 |

Example 7

Analyte Sensor 1 was exposed to bromobenzene. The fluorescence signal was measured using Test Method 1. The emission intensity at the peak maximum was recorded as a function of time and is shown in Table 7.

TABLE 7

| Scan # | Time (min) | Intensity Peak Maximum |
| --- | --- | --- |
| 1 | 0 | 2637132 |
| 2 | 0.5 | 4930718 |
| 3 | 3.5 | 6503325 |
| 4 | 7.5 | 6808921 |
| 5 | 14.5 | 6901736 |
| 6 | 28.5 | 6972673 |

Example 8

Analyte Sensor 1 was exposed to heptane. The fluorescence signal was measured using Test Method 1. The emission intensity at the peak maximum was recorded as a function of time and is shown in Table 8.

TABLE 8

| Scan # | Time (min) | Intensity Peak Maximum |
| --- | --- | --- |
| 1 | 0 | 3611291 |
| 2 | 0.5 | 1883704 |
| 3 | 3.5 | 2305960 |
| 4 | 7.5 | 2550904 |
| 5 | 14.5 | 2811781 |
| 6 | 28.5 | 3090652 |

Example 9

Analyte Sensor 1 was exposed to mesitylene. The fluorescence signal was measured using Test Method 1. The emission intensity at the peak maximum was recorded as a function of time and is shown in Table 9.

TABLE 9

| Scan # | Time (min) | Intensity Peak Maximum |
| --- | --- | --- |
| 1 | 0 | 6653578 |
| 2 | 0.5 | 12560826 |
| 3 | 3.5 | 16347323 |
| 4 | 7.5 | 17592583 |
| 5 | 14.5 | 17802300 |
| 6 | 28.5 | 16922620 |

Example 10

Analyte Sensor 2 was exposed to ethyl acetate. The fluorescence signal was measured using Test Method 2. The emission intensity at the peak maximum was recorded as a function of time and is shown in Table 10.

TABLE 10

| Scan # | Time (min) | Intensity Peak Maximum |
| --- | --- | --- |
| 1 | 0 | 940000 |
| 2 | 7 | 1190000 |
| 3 | 8 | 1320000 |
| 4 | 10 | 1410000 |
| 5 | 11 | 1480000 |
| 6 | 13 | 1540000 |
| 7 | 14 | 1600000 |
| 8 | 19 | 1700000 |
| 9 | 21 | 1730000 |

Example 11

Analyte Sensor 2 was exposed to acetone. The fluorescence signal was measured using Test Method 2. The emission intensity at the peak maximum was recorded as a function of time and is shown in Table 11.

TABLE 11

| Scan # | Time (min) | Intensity Peak Maximum |
| --- | --- | --- |
| 1 | 0 | 5730000 |
| 2 | 5 | 6570000 |
| 3 | 7 | 7550000 |
| 4 | 8 | 8340000 |
| 5 | 10 | 8830000 |
| 6 | 11 | 9030000 |
| 7 | 13 | 9190000 |
| 8 | 14 | 9280000 |
| 9 | 20 | 9341409 |

Example 12

Analyte Sensor 2 was exposed to methyl ethyl ketone. The fluorescence signal was measured using Test Method 2. The emission intensity at the peak maximum was recorded as a function of time and is shown in Table 12.

TABLE 12

| Scan # | Time (min) | Intensity Peak Maximum |
|---|---|---|
| 1 | 0 | 2130000 |
| 2 | 4 | 3170000 |
| 3 | 6 | 3460000 |
| 4 | 7 | 3640000 |
| 5 | 9 | 3800000 |

Example 13

Analyte Sensor 2 was exposed to isopropyl alcohol. The fluorescence signal was measured using Test Method 2. The emission intensity at the peak maximum was recorded as a function of time and is shown in Table 13.

TABLE 13

| Scan # | Time (min) | Intensity Peak Maximum |
|---|---|---|
| 1 | 0 | 2320000 |
| 2 | 9 | 2280000 |
| 3 | 10 | 2610000 |
| 4 | 12 | 3000000 |
| 5 | 14 | 3190000 |
| 6 | 15 | 3250000 |
| 7 | 17 | 3340000 |
| 8 | 20 | 3370000 |

Example 14

Analyte Sensor 2 was exposed to tripropyl amine. The fluorescence signal was measured using Test Method 2. The emission intensity at the peak maximum was recorded as a function of time and is shown in Table 14.

TABLE 14

| Scan # | Time (min) | Intensity Peak Maximum |
|---|---|---|
| 1 | 0 | 3830000 |
| 2 | 3 | 3370000 |
| 3 | 5 | 3350000 |
| 4 | 6 | 3330000 |
| 5 | 8 | 3320000 |
| 6 | 9 | 3310000 |
| 7 | 12 | 3290000 |

Example 15

Analyte Sensor 2 was exposed to chloroform. The fluorescence signal was measured using Test Method 2. The emission intensity at the peak maximum was recorded as a function of time and is shown in Table 15.

TABLE 15

| Scan # | Time (min) | Intensity Peak Maximum |
|---|---|---|
| 1 | 0 | 3952820 |
| 2 | 0.5 | 5512990 |
| 3 | 1.5 | 5517250 |
| 4 | 3.5 | 5418280 |
| 5 | 4.5 | 5349140 |

Example 16

Analyte Sensor 2 was exposed to acetonitrile. The fluorescence signal was measured using Test Method 2. The emission intensity at the peak maximum was recorded as a function of time and is shown in Table 16.

TABLE 16

| Scan # | Time (min) | Intensity Peak Maximum |
|---|---|---|
| 1 | 0 | 2506560 |
| 2 | 0.5 | 2932280 |
| 3 | 2.5 | 2902410 |
| 4 | 3.5 | 2819460 |
| 5 | 6.5 | 2675280 |
| 6 | 8.5 | 2556610 |

We claim:

1. A method for detecting the presence or absence of an organic vapor, the method comprising providing an analyte sensor comprising a polymeric material having a unit of Formula I

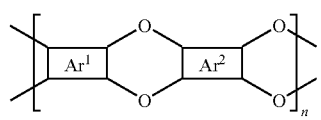

I wherein the polymeric material having the unit of Formula I is a reaction product of a first aromatic compound and a second aromatic compound such that $Ar^1$ and $Ar^2$ are each fused to a common 1,4-dioxane ring;

$Ar^1$ comprises a first aromatic group that is planar or generally planar;

$Ar^2$ comprises a second aromatic group and a third aromatic group connected to the second aromatic group through a contortion site such that the second aromatic group and the third aromatic group are not in the same plane; and n is an integer equal to or greater than 1;

exposing the analyte sensor to an environment that may contain an organic vapor; and monitoring the analyte sensor for a change in a fluorescence signal in the visible region of the electromagnetic spectrum upon exposure to the environment, wherein a change in the fluorescence signal indicates exposure to the organic vapor.

2. The method of claim 1, wherein the organic vapor does not emit a fluorescence signal in the visible region of the electromagnetic spectrum.

3. The method of claim 1, wherein the polymeric material having the unit of Formula I is porous and sorbs the organic vapor.

4. The method of claim 1, wherein the polymeric material having the unit of Formula I has a surface area of at least 300 $m^2/g$ as measured by nitrogen adsorption.

5. The method of claim 1, wherein the change in the fluorescence signal is proportional to a concentration of the organic vapor.

6. The method of claim 1, wherein the first aromatic compound has at least four halogen groups and the second aromatic compound has at least four hydroxy groups, the first aromatic compound selected from

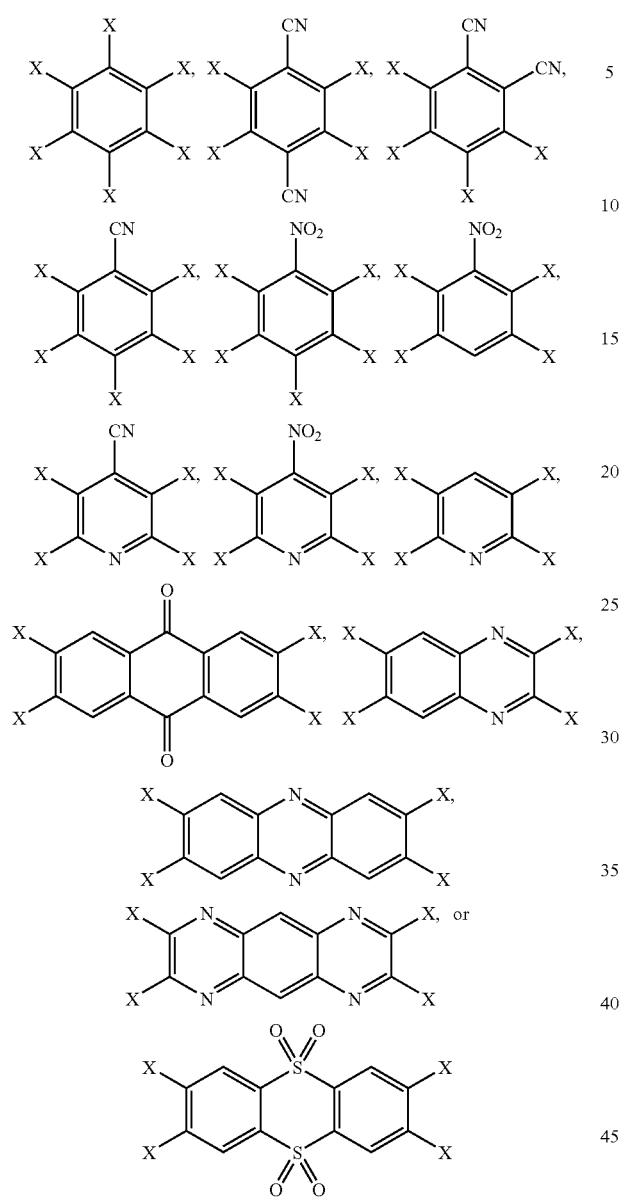
where X is a halogen group.
7. The method of claim 6, wherein the second aromatic compound is selected from
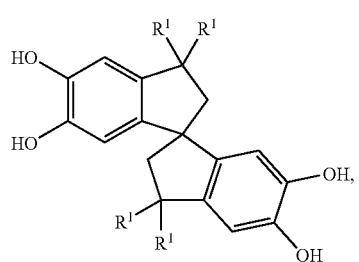
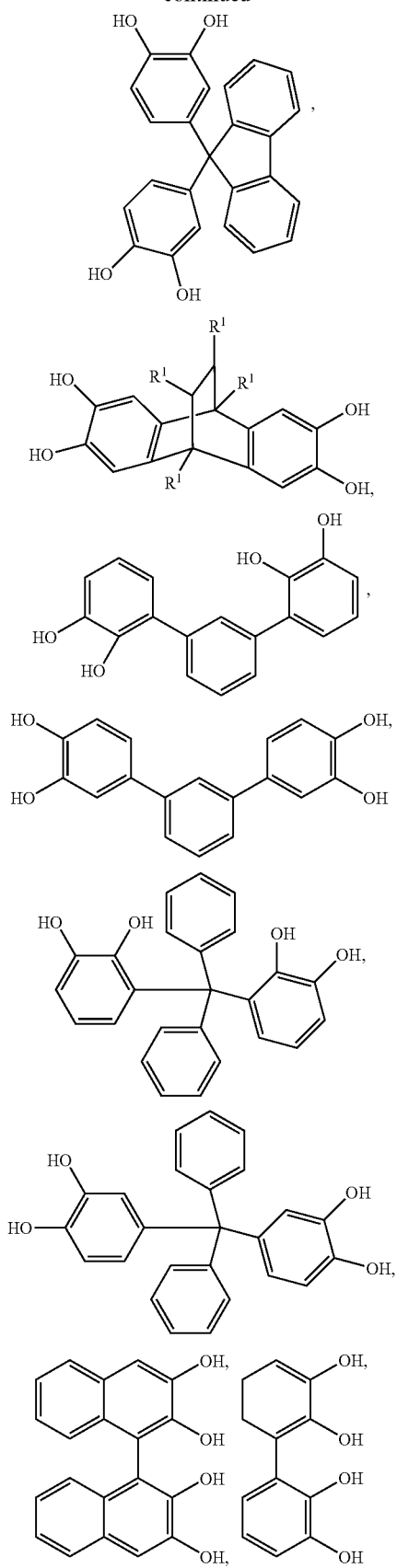

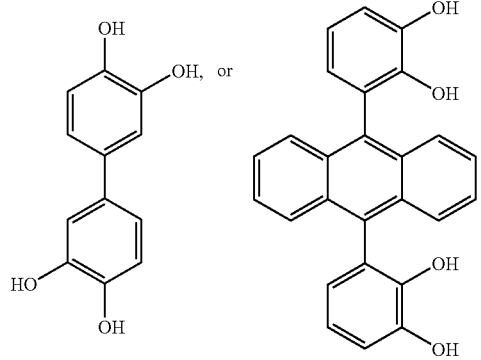

where R¹ is hydrogen or an alkyl.

8. The method of claim 6, wherein the second aromatic compound is of formula

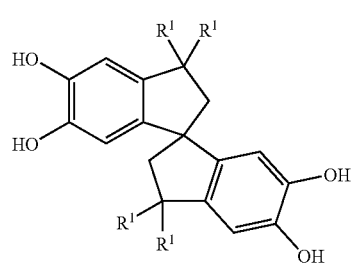

where R¹ is hydrogen or alkyl.

9. The method of claim 1, wherein the first aromatic compound has at least four hydroxy groups and the second aromatic compound has at least four halogen groups, wherein the first aromatic compound is selected from

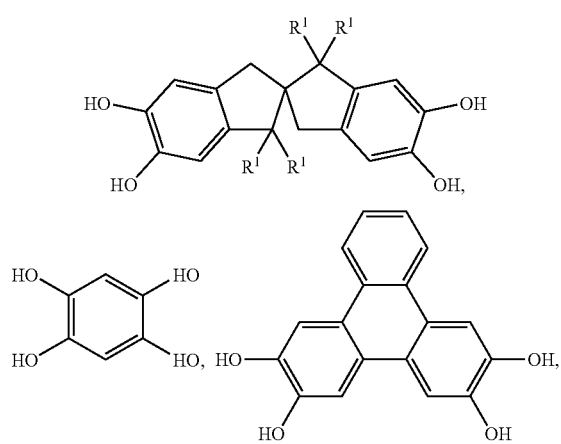

where R¹ is hydrogen or an alkyl.

10. The method of claim 9, wherein the second aromatic compound is

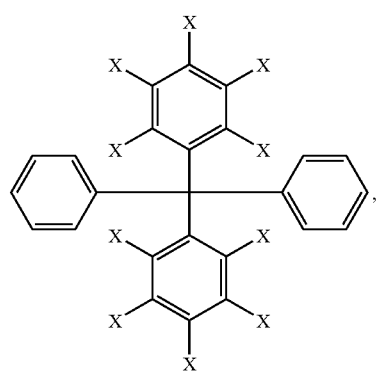

where X is a halo.

11. The method of claim 1, wherein the polymeric material having the unit of Formula I is in a form of a film or coating.

12. The method of claim 1, wherein the change in the fluorescence signal is an increase in the fluorescence signal resulting from exposure to an organic vapor comprising a ketone, ether, alkane, halogenated alkane, ester, aldehyde, alcohol, nitrile, benzene, or benzene substituted with a substituent selected from alkyl, halogen or a combination thereof.

13. The method of claim 1, wherein the change in the fluorescence signal is an increase in the fluorescence signal resulting from exposure to an organic vapor comprising an organic compound lacking an amino group or a nitro group.

14. The method of claim 1, wherein the change in the fluorescence signal is a decrease in the fluorescence signal resulting from exposure to an organic vapor comprising an organic compound having a nitro group or amino group.

15. The method of claim 1, wherein the analyte sensor further comprises a support substrate adjacent to the polymeric material having the unit of Formula I.

16. The method of claim 15, wherein the support substrate has a reflective surface.

17. The method of claim 1, wherein monitoring the analyte sensor for a change in the fluorescence signal comprises (a) measuring a reference fluorescence signal prior to exposing the analyte sensor to the environment, (b) measuring a sample fluorescence signal after exposing the same analyte sensor to the sample, and (c) subtracting the reference fluorescence signal from the sample fluorescence signal.

18. The method of claim 1, wherein monitoring the analyte sensor for a change in the fluorescence signal comprises (a) measuring a reference fluorescence signal prior to exposing the analyte sensor to the environment, (b) measuring a sample fluorescence signal after exposing the same analyte sensor to the sample, and (c) dividing the sample fluorescence signal by the reference fluorescence signal.

19. The method of claim 1, wherein the method further comprises providing a reference sensor similar to the analyte sensor and wherein monitoring the analyte sensor for a change in fluorescence signal comprises (a) measuring a reference fluorescence signal for the reference sensor that is not exposed to the environment, (b) measuring a sample fluorescence signal after exposing the analyte sensor to the sample, and (c) subtracting the reference fluorescence signal from the sample fluorescence signal.

20. The method of claim 1, wherein the method further comprises providing a reference sensor similar to the analyte sensor and wherein monitoring the analyte sensor for a change in fluorescence signal comprises (a) measuring a reference fluorescence signal for the reference sensor that is not exposed to the environment, (b) measuring a sample fluorescence signal after exposing the analyte sensor to the sample, and (c) dividing the sample fluorescence signal by the reference fluorescence signal.

* * * * *

UNITED STATES PATENT AND TRADEMARK OFFICE
CERTIFICATE OF CORRECTION

PATENT NO.       : 7,704,751 B2
APPLICATION NO.  : 11/552825
DATED            : April 27, 2010
INVENTOR(S)      : Michael C Palazzotto et al.

Page 1 of 2

It is certified that error appears in the above-identified patent and that said Letters Patent is hereby corrected as shown below:

Column 4
Line 11, delete "IIf," and insert -- IIf; --, therefor.

Column 5
Line 48 (Approx.), delete "III:" and insert -- III; --, therefor.

Column 9
Line 2, delete "anthracen-diyl" and insert -- anthracene-diyl --, therefor.

Column 11
Line 16 (Approx.), delete "anthaquinone" and insert -- anthraquinone --, therefor.

Column 14
Line 5, delete "Barret," and insert -- Barrett, --, therefor.

Column 27 (Structure)

Line 60-65, in Claim 9, delete " 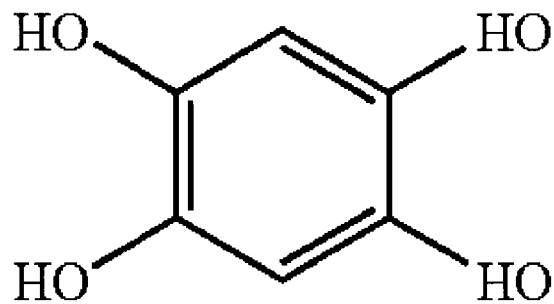 , " and insert

Signed and Sealed this
Thirtieth Day of August, 2011

David J. Kappos
*Director of the United States Patent and Trademark Office*

CERTIFICATE OF CORRECTION (continued)
U.S. Pat. No. 7,704,751 B2

-- 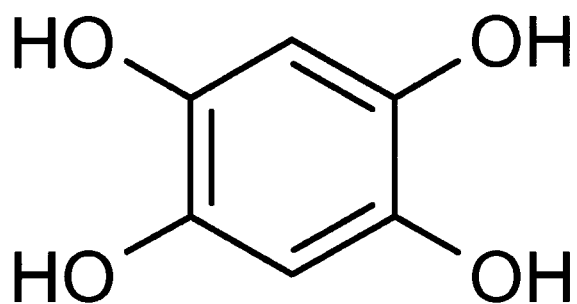 --, therefor.